United States Patent
Zhang et al.

(10) Patent No.: US 6,514,972 B2
(45) Date of Patent: Feb. 4, 2003

(54) HETEROPOLYCYCLIC INHIBITORS OF PROTEIN KINASES

(75) Inventors: Zaihui Zhang, Richmond (CA); Xinyao Du, Richmond (CA); Serguei Sviridov, Burnaby (CA); Greg Chopiuk, Vancouver (CA)

(73) Assignee: Kinetek Pharmaceuticals, Inc., Vancouver (CA)

( * ) Notice: Subject to any disclaimer, the term of this patent is extended or adjusted under 35 U.S.C. 154(b) by 0 days.

(21) Appl. No.: 09/900,073

(22) Filed: Jul. 6, 2001

(65) Prior Publication Data
US 2002/0035251 A1 Mar. 21, 2002

Related U.S. Application Data

(63) Continuation-in-part of application No. 09/611,038, filed on Jul. 6, 2000, now abandoned.
(51) Int. Cl.[7] ........... C07D 487/04; A61K 31/53; A61K 31/4985; A61P 35/00; A61P 17/06
(52) U.S. Cl. ........... 514/243; 544/183; 544/184; 544/342; 544/343; 514/250
(58) Field of Search ............... 544/342, 343, 544/183, 184; 514/243, 250

(56) References Cited

U.S. PATENT DOCUMENTS

| | | | |
|---|---|---|---|
| 5,221,627 A | 6/1993 | Grigg et al. | 436/89 |
| 5,789,427 A | 8/1998 | Chen et al. | 514/352 |

OTHER PUBLICATIONS

Junek et al., *Syntheses with nitriles, XLV. 2–(1, 3–Dioxo–2–indanylidene) benzimidazoline–and isomer of indigo*, Inst. Org. Chem., 1977, 2276–82, 110(6), Univ. Graz, Graz, Austria (Abstract From STN—CAS).

Kane et al. (1999), "Induction of NF–κB by the Akt/PKB Kinase." *Current Biology*, vol. 9:601–604.

*Primary Examiner*—Mark L. Berch
*Assistant Examiner*—Kahsay Habte
(74) *Attorney, Agent, or Firm*—Pamela J. Sherwood; Bozicevic, Field & Francis LLP; David W. Parker

(57) ABSTRACT

A compound of the formula

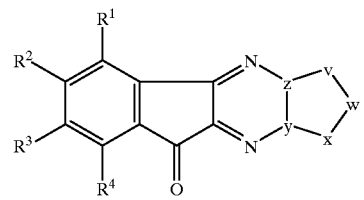

wherein, independently at each occurrence, v, w, and x are selected from C, N, O, and S, with H substitution as needed to fulfill open valence sites; y and z are selected from N and C, with H substitution as needed to fulfill open valence sites, with the proviso that each of w, v, x, y and z is not simultaneously C; the ring formed from v, w, x, y and z may be saturated or unsaturated; and $R^1$, $R^2$, $R^3$ and $R^4$ are selected from hydrogen, alkyl, aryl, alkaryl, aralkyl, heteroalkyl, and heteroaryl; wherein any adjacent two of $R^1$, $R^2$, $R^3$ and $R^4$ may join together to form a 5, 6 or 7-membered carbocyclic or heterocyclic ring, with the proviso that each of $R^1$, $R^2$, $R^3$ and $R^4$ is not simultaneously hydrogen. Pharmaceutical compositions of said compounds, and methods of use in the treatment of biological conditions including cellular hyperproliferation, are disclosed.

39 Claims, No Drawings

HETEROPOLYCYCLIC INHIBITORS OF PROTEIN KINASES

CROSS REFERENCE OF PRIOR APPLICATION

This application is a continuation-in-part of U.S. patent application Ser. No. 09/611,038, filed Jul. 6, 2000, now abandoned, which application is incorporated herein by reference in entirety.

BACKGROUND OF THE INVENTION

Protein phosphorylation is a fundamental process for the regulation of cellular functions. The coordinated action of both protein kinases and phosphatases controls the levels of phosphorylation and, hence, the activity of specific target proteins. One of the predominant roles of protein phosphorylation is in signal transduction, where extracellular signals are amplified and propagated by a cascade of protein phosphorylation and dephosphorylation events.

Signal transduction also plays a key regulatory role in the growth and metastatic potential of tumor cells. These signaling pathways form an interconnecting grid that serves to regulate the homeostatic, survival and invasive functions of the cell. Among the key regulatory molecules in these pathways are the serine/threonine-protein kinases cyclic AMP-dependent protein kinase (PKA), Akt (PKB) and protein kinase C (PKC). These protein kinases modulate pathways associated with tumor proliferation, cell survival and multidrug resistance, and at a molecule level are likely to serve as effective targets for drug design.

SUMMARY OF THE INVENTION

Pharmaceutical compositions and compounds are provided. The compounds of the invention are heteropolycyclic compounds. In one embodiment of the invention, formulations of the compounds in combination with a physiologically acceptable carrier are provided. The pharmaceutical formulations are useful in the treatment of disorders associated with hyperproliferation, and responses to insulin signaling.

For example, in one aspect, the present invention provides compounds having the formula

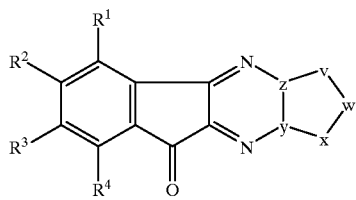

wherein, independently at each occurrence, v, w, and x are selected from C, N, O, and S, with H substitution as needed to fulfill open valence sites; y and z are selected from N and C, with H substitution as needed to fulfill open valence sites, with the proviso that each of w, v, x, y and z is not simultaneously C; the ring formed from v, w, x, y and z may be saturated or unsaturated; and $R^1$, $R^2$, $R^3$ and $R^4$ are selected from hydrogen, alkyl, aryl, alkaryl, aralkyl, heteroalkyl, and heteroaryl; wherein any adjacent two of $R^1$, $R^2$, $R^3$ and $R^4$ may join together to form a 5, 6 or 7-membered carbocyclic or heterocyclic ring, with the proviso that each of $R^1$, $R^2$, $R^3$ and $R^4$ is not simultaneously hydrogen.

In another aspect, the present invention provides a pharmaceutical composition comprising a pharmaceutically acceptable carrier, excipient or diluent, and a compound of the formula

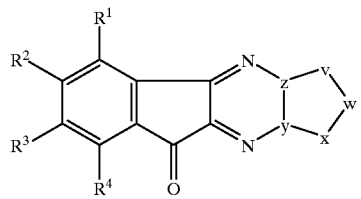

wherein, independently at each occurrence, v, w, and x are selected from C, N, O, and S, with H substitution as needed to fulfill open valence sites; y and z are selected from N and C, with H substitution as needed to fulfill open valence sites, with the proviso that each of w, v, x, y and z is not simultaneously C; the ring formed from v, w, x, y and z may be saturated or unsaturated; and $R^1$, $R^2$, $R^3$ and $R^4$ are selected from hydrogen, alkyl, aryl, alkaryl, aralkyl, heteroalkyl, and heteroaryl; wherein any adjacent two of $R^1$, $R^2$, $R^3$ and $R^4$ may join together to form a 5, 6 or 7-membered carbocyclic or heterocyclic ring. In an optional embodiment, each of $R^1$, $R^2$, $R^3$ and $R^4$ is not simultaneously hydrogen.

DETAILED DESCRIPTION OF THE INVENTION

The present invention provides novel heteropolycyclic fused ring compounds, compositions and methods as set forth within this specification. In general, all technical and scientific terms used herein have the same meaning as commonly understood to one of ordinary skill in the art to which this invention belongs, unless clearly indicated otherwise. For clarification, listed below are definitions for certain terms used herein to describe the present invention. These definitions apply to the terms as they are used throughout this specification, unless otherwise clearly indicated.

DEFINITION OF TERMS

As used herein the singular forms "a", "and", and "the" include plural referents unless the context clearly dictates otherwise. For example, "a compound" refers to one or more of such compounds, "a group" refers to one or more of such groups, etc., while "the enzyme" includes a particular enzyme as well as other family members and equivalents thereof as known to those skilled in the art.

"Acyl" is a heteroalkyl wherein a terminal carbon of the heteroalkyl group is in the form of a carbonyl group, i.e., (alkyl or heteroalkyl)-C=O, where examples include acetyl ($CH_3$—(C=O)—).

"Alkaryl" is another name for alkylarylene, wherein an alkyl group is bonded to an arylene group, and the arylene group is bonded to the remainder of the molecule. Tolyl ($CH_3$-phenyl-) and xylyl (($CH_3$)$_2$-phenyl-) are representative alkaryl groups. Thus, in compounds of the present invention, any of $R^1$, $R^2$, $R^3$ and $R^4$ may be alkaryl.

"Alkenyl" is an alkyl group, where an alkenyl group has at least one carbon—carbon double bond.

"Alkyl" is a monovalent, saturated or unsaturated, straight, branched or cyclic, aliphatic (i.e., not aromatic) hydrocarbon group. In various embodiments of the present invention, the alkyl group has 1–20 carbon atoms, i.e., is a C1–C20 group (i.e., is a $C_1$–$C_{20}$ group), or is a C1–C18 group, a C1–C12 group, a C1–C6 group, or a C1–C4 group. Independently, in various embodiments of the present invention, the alkyl group: has zero branches (i.e., is a straight chain), one branch, two branches, or more than two branches; is saturated; is unsaturated (where an unsaturated alkyl group may have one double bond, two double bonds, more than two double bonds, and/or one triple bond, two triple bonds, or more than two triple bonds); is, or includes, a cyclic structure; is acyclic. Exemplary alkyl groups include $C_1$alkyl (i.e., —$CH_3$ (methyl)), $C_2$alkyl (i.e., —$CH_2CH_3$ (ethyl), —CH=$CH_2$ (ethenyl) and —C≡CH (ethynyl)) and $C_3$alkyl (i.e., —$CH_2CH_2CH_3$ (n-propyl), —CH($CH_3$)$_2$ (i-propyl), —CH=CH—$CH_3$ (1-propenyl), —C≡C—$CH_3$ (1-propynyl), —$CH_2$—CH=$CH_2$ (2-propenyl), —$CH_2$—C≡CH (2-propynyl), —C($CH_3$)=$CH_2$ (1-methylethenyl), and —CH($CH_2$)$_2$ (cyclopropyl)), which identify specific lower alkyl groups. Thus, in compounds of the present invention, any of $R^1$, $R^2$, $R^3$ and $R^4$ may be alkyl.

"Alkylene" is a polyvalent, saturated or unsaturated, straight, branched or cyclic, aliphatic (i.e., not aromatic) hydrocarbon group. In various embodiments, the alkylene group has 1–20 carbon atoms, i.e., is a C1–C20 group, or is a C1–C18 group, a C1–C12 group, a C1–C6 group, or a C1–C4 group. Independently, in various embodiments, the alkylene group: has zero branches (i.e., is a straight chain), one branch, two branches, or more than two branches; is saturated; is unsaturated (where an unsaturated alkylene group may have one double bond, two double bonds, more than two double bonds, and/or one triple bond, two triple bonds, or more than three triple bonds); is or contains a cyclic group; is acyclic; is divalent, i.e., has two open sites that each bond to a non-alkylene group; is trivalent, i.e., has three open sites that each bond to a non-alkylene group; has more than three open sites. Exemplary alkylene groups include $C_1$alkylene (i.e., —$CH_2$—) and $C_2$alkylene (i.e., —$CH_2CH_2$—, —CH=CH—, —C≡C—, —C(=$CH_2$)—, and —CH($CH_3$)—).

"Aralkyl" is another name for arylalkylene, wherein at least one of the open bonding sites of an alkylene group is bonded to an aryl group, where benzyl is an example. Thus, in compounds of the present invention, any of $R^1$, $R^2$, $R^3$ and $R^4$ may be aralkyl.

"Aryl" is a monovalent, aromatic, hydrocarbon, ring system. The ring system may be monocyclic or fused polycyclic (e.g., bicyclic, tricyclic, etc.). In various embodiments of the present invention, the monocyclic aryl ring is C5–C10, or C5–C7, or C5–C6, where these carbon numbers refer to the number of carbon atoms that form the aryl ring system. A C6 ring system, i.e., a phenyl ring, is a preferred aryl group. In various embodiments, the polycyclic ring is a bicyclic aryl group, where preferred bicyclic aryl groups are C8–C12, or C9–C10. A naphthyl ring, which has 10 carbon atoms, is a preferred polycyclic aryl group. Thus, in compounds of the present invention, any of $R^1$, $R^2$, $R^3$ and $R^4$ may be aryl.

"Arylene" is a polyvalent, aromatic hydrocarbon, ring system. The ring system may be monocyclic or fused polycyclic (e.g., bicyclic, tricyclic, etc.). In various embodiments, the monocyclic arylene group is C5–C10, or C5–C7, or C5–C6, where these carbon numbers refer to the number of carbon atoms that form the ring system. A C6 ring system, i.e., a phenylene ring, is a preferred aryl group. In various embodiments, the polycyclic ring is a bicyclic arylene group, where preferred bicyclic arylene groups are C8–C12, or C9–C10. A naphthylene ring, which has 10 carbon atoms, is a preferred polycyclic aryl group. The arylene group may be divalent, i.e., it has two open sites that each bond to another group; or trivalent, i.e., it has three open sites that each bond to another group; or it may have more than three open sites.

"Carbocyclic" refers to a ring formed entirely of carbon. A carbocyclic group, also referred to as a carbocyclic ring, may be saturated or unsaturated. The ring may be unsaturated to the point of being aromatic.

"Cycloalkenyl" is an alkyl group where a cycloalkenyl group is a cyclic hydrocarbon group with at least one double bond.

"Cycloalkenylene" is an alkylene group which is a cyclic hydrocarbon with at least one double bond and with at least two bonding sites.

"Cycloalkyl" is an alkyl group, where a cycloalkyl is a cyclic hydrocarbon group.

"Cycloalkylalkylene" is an alkyl group wherein at least one open bonding site of an alkylene group is joined to a cycloalkyl group.

"Cycloalkylene" is an alkylene group which is a cyclic hydrocarbon group with at least two open bonding sites.

"Cycloalkylenealkylene" is an alkylene group wherein a cycloalkylene group is bonded to a non-cyclic alkylene group, and each of the cycloalkylene and non-cyclic alkylene group have at least one open bonding site.

"Haloalkyl" is a heteroalkyl wherein at least one carbon of an alkyl group is bonded to at least one halogen.

"Halogen" is a heteroalkyl wherein a methyl group is replaced with a heteroatom selected from fluorine, chlorine, bromine and iodine. Fluorine and chlorine are preferred halogens in compounds and compositions of the present invention.

"Heteroalkyl" is an alkyl group (as defined herein) wherein at least one of the carbon atoms of an alkyl group (or perhaps the sole carbon atom of an alkyl group) is replaced with a heteroatom. Preferred heteroatoms are nitrogen, oxygen, sulfur, and halogen. A heteroatom may, but typically does not, have the same number of valence sites as carbon. Accordingly, when a carbon is replaced with a heteroatom, the number of hydrogens bonded to the heteroatom may need to be increased or decreased to match the number of valence sites of the heteroatom. For instance, if carbon (valence of four) is replaced with nitrogen (valence of three), then one of the hydrogens formerly attached to the replaced carbon must be deleted. Likewise, if carbon is replaced with halogen (valence of one), then three (i.e., all) of the hydrogens formerly bonded to the replaced carbon must be deleted. Thus, in compounds of the present invention, any of $R^1$, $R^2$, $R^3$ and $R^4$ may be heteroalkyl.

"Heteroaryl" is a monovalent aromatic ring system containing carbon and at least one heteroatom in the ring. The heteroaryl group may, in various embodiments of the present invention, have one heteroatom, or 1–2 heteroatoms, or 1–3 heteroatoms, or 1–4 heteroatoms in the ring. Heteroaryl rings may be monocyclic or polycyclic, where the polycyclic ring may contain fused, spiro or bridged ring junctions. In one embodiment, the heteroaryl is selected from monocyclic and bicyclic. Monocyclic heteroaryl rings may contain from about 5 to about 10 member atoms (carbon and heteroatoms), preferably from 5–7, and most preferably from 5–6 member atoms in the ring. Bicyclic heteroaryl rings may contain from about 8–12 member atoms, or 9–10 member atoms in the ring. The heteroaryl ring may be unsubstituted or substituted. In one embodiment, the heteroaryl ring is unsubstituted. In another embodiment, the heteroaryl ring is substituted. Exemplary heteroaryl groups include benzofuran, benzothiophene, furan, imidazole, indole, isothiazole, oxazole, piperazine, pyrazine, pyrazole, pyridazine, pyridine, pyrimidine, pyrrole, quinoline, thiadiazole, thiazole and thiophene. Thus, in compounds of the present invention, any of $R^1$, $R^2$, $R^3$ and $R^4$ may be heteroaryl.

"Heteroatom" is a halogen, nitrogen, oxygen, silicon or sulfur atom. Groups containing more than one heteroatom may contain different heteroatoms.

"Heterocyclic" refers to a ring formed from one or more non-carbon atoms. The heterocyclic group, also referred to as the heterocyclic ring, may contain or include carbon, however, carbon is not the only ring atom present in the heterocyclic ring. Other atoms that may be part of the heterocyclic ring are nitrogen, sulfur and oxygen.

"Halohydrocarbyl" refers to hydrocarbyl group wherein at least one, and possibly all, of the hydrogen atoms are substituted with halogen atoms, the halogen atoms being independently selected at each occurence.

"Hydrocarbyl" refers to a chemical moiety containing only carbon and hydrogen atoms. The moiety may be, e.g., an alkyl or aryl group, e.g., methyl or phenyl. In one aspect of the invention, a hydrocarbyl group contains 1–15 carbon, while in another aspect the hydrocarbyl contains 1–10 carbons, while in yet another aspect the hydrocarbyl contains 1–6 carbons.

For clarification, the term "independently at each occurrence" means that each selection is made independently of every other selection, so that no one selection impacts on any other selection, so long as a stable compound results.

As used herein, the term "compound" shall refer to and encompass the chemical compound itself as well as, where applicable: amorphous and crystalline forms of the compound, including polymorphic forms, said forms in mixture or in isolation; free acid and free base forms of the compound; isomers of the compound, including geometric isomers, optical isomers, and tautomeric isomers, said optical isomers to include enantiomers and diastereomers, chiral isomers and non-chiral isomers, said optical isomers to include isolated optical isomers or mixtures of optical isomers including racemic and non-racemic mixtures; said geometric isomers to include transoid and cisoid forms, where an isomer may be in isolated form or in admixture with one or more other isomers; isotopes of the compound, including deuterium- and tritium-containing compounds, and including compounds containing radioisotopes, including therapeutically- and diagnostically-effective radioisotopes; multimeric forms of the compound, including dimeric, trimeric, etc. forms; salts of the compound, including acid addition salts and base addition salts, including organic counterions and inorganic counterions, and including zwitterionic forms, where if a compound is associated with two or more counterions, the two or more counterions may be the same or different; and solvates of the compound, including hemisolvates, monosolvates, disolvates, etc., including organic solvates and inorganic solvates, said inorganic solvates including hydrates; where if a compound is associated with two or more solvent molecules, the two or more solvent molecules may be the same or different.

Salts of compounds of the present invention are preferably pharmaceutically acceptable salts, and are preferably acid addition salts. "Pharmaceutically acceptable salt" and "salts thereof" in the compounds of the present invention refers to acid addition salts and base addition salts.

Acid addition salts refer to those salts formed from compounds of the present invention and inorganic acids such as hydrochloric acid, hydrobromic acid, sulfuric acid, nitric acid, phosphoric acid and the like, and/or organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

Base addition salts refer to those salts formed from compounds of the present invention and inorganic bases such as sodium, potassium, lithium, ammonium, calcium, magnesium, iron, zinc, copper, manganese, aluminum salts and the like. Suitable salts include the ammonium, potassium, sodium, calcium and magnesium salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethamine, dicyclohexylamine, lysine, arginine, histidine, caffeine, procaines, hydrabamine, choline, betaine, ethylenediamine, glucosamine, methylglucamine, theobromine, purines, piperazine, piperidine, N-ethylpiperidine, and the like.

As standard in organic chemistry, the designations C, N, O, S and H represent carbon, nitrogen, oxygen, sulfur and hydrogen, respectively.

In one aspect, the present invention provides a compound of the formula 1

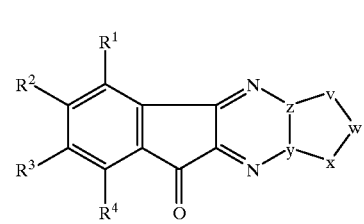

(1)

wherein, independently at each occurrence, v, w, and x are selected from C, N, O, and S, with H substitution as needed to fulfill open valence sites; y and z are selected from N and C, with the proviso that each of w, v, x, y and z is not simultaneously C; the ring formed from v, w, x, y and z may be saturated or unsaturated; and $R^1$, $R^2$, $R^3$ and $R^4$ are selected from hydrogen, alkyl, aryl, alkaryl, aralkyl, heteroalkyl, and heteroaryl; wherein any adjacent two of $R^1$, $R^2$, $R^3$ and $R^4$ may join together to form a 5, 6 or 7-membered carbocyclic or heterocyclic ring, with the proviso that each of $R^1$, $R^2$, $R^3$ and $R^4$ is not simultaneously hydrogen.

Thus, as to $R^1$, $R^2$, $R^3$ and $R^4$, each of these designations is independently selected from hydrogen, alkyl, aryl, alkaryl, aralkyl, heteroalkyl, and heteroaryl; wherein any adjacent two of $R^1$, $R^2$, $R^3$ and $R^4$ may join together to form a 5, 6 or 7-membered carbocyclic or heterocyclic ring, with the proviso that each of $R^1$, $R^2$, $R^3$ and $R^4$ is not simultaneously hydrogen. The terms alkyl, aryl, alkaryl, aralkyl, heteroalkyl, and heteroaryl have been defined above. In one aspect of the present invention, $R^1$, $R^2$, $R^3$ and $R^4$ are each selected from hydrogen, $C_1$–$C_6$alkyl and $C_1$–$C_6$heteroalkyl. In another aspect of the invention, at least one of $R^1$, $R^2$, $R^3$ and $R^4$ is a heteroalkyl group selected from groups of the formula $R^5$—O— and $R^5$—S— wherein $R^5$ is a $C_1$–$C_{15}$, preferably a $C_1$–$C_{10}$, more preferably a $C_1$–$C_6$ hydrocarbyl or heteroalkyl. In another aspect, at least one of $R^1$, $R^2$, $R^3$ and $R^4$ is a heteroalkyl group selected from fluorine, chlorine, bromine and iodine. In another aspect, at least one of $R^1$, $R^2$, $R^3$ and $R^4$ is an alkyl group selected from $C_1$–$C_{15}$alkyl, while in another aspect the alkyl group is selected from $C_1$–$C_6$alkyl.

In another aspect of the invention, two adjacent $R^1$, $R^2$, $R^3$ and $R^4$ join together to form a 5, 6 or 7-membered carbocyclic or heterocyclic ring. In another aspect of the invention, two adjacent $R^1$, $R^2$, $R^3$ and $R^4$ join together to form a 5, 6 or 7-membered carbocyclic ring. For example, the present invention provides compounds of the formula

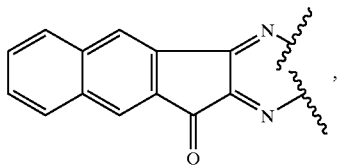

where the wiggly lines represent the ring formed from v, w, x, y and z.

In another aspect, the invention provides a compound of the formula 1

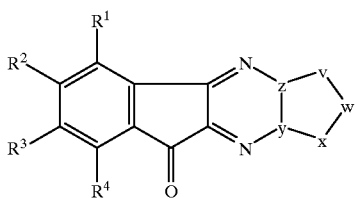

(1)

wherein, independently at each occurrence, v, w, and x are selected from C, N, O, and S, with H substitution as needed to fulfill open valence sites; y and z are selected from N and C, with the proviso that each of w, v, x, y and z is not simultaneously C; the ring formed from v, w, x, y and z may be saturated or unsaturated; and $R^1$, $R^2$, $R^3$ and $R^4$ are selected from hydrogen and C1–C15 hydrocarbyl or halohydrocarbyl groups, wherein any adjacent two of $R^1$, $R^2$ $R^3$ and $R^4$ may join together to form a 5, 6 or 7-membered carbocyclic ring, with the proviso that each of $R^1$, $R^2$, $R^3$ and $R^4$ is not simultaneously hydrogen. In one aspect, the $R^1$, $R^2$, $R^3$ and $R^4$ groups are selected from $C_1$–$C_{10}$ hydrocarbyl and halohydrocarbyl groups. In another aspect, the $R^1$, $R^2$, $R^3$ and $R^4$ groups are selected from C1–C6 hydrocarbyl and halohydrocarbyl groups.

In another aspect, the invention provides a compound of the formula 1

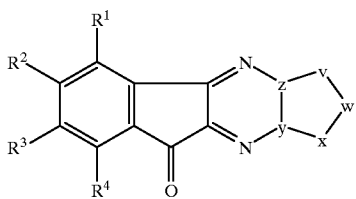

(1)

wherein, independently at each occurrence, v, w, and x are selected from C, N, O, and S, with H substitution as needed to fulfill open valence sites; y and z are selected from N and C, with the proviso that each of w, v, x, y and z is not simultaneously C; the ring formed from v, w, x, y and z may be saturated or unsaturated; and $R^1$, $R^2$, $R^3$ and $R^4$ are selected from hydrogen and $R^6$, $R^7$, and $R^8$, where $R^6$ is selected from alkyl, heteroalkyl, aryl and heteroaryl; $R^7$ is selected from $(R^6)_n$-alkylene, $(R^6)_n$-heteroalkylene, $(R^6)_n$-arylene and $(R^6)_n$-heteroarylene; $R^8$ is selected from $(R^7)_n$-alkylene, $(R^7)_n$-heteroalkylene, $(R^7)_n$-arylene, and $(R^7)_n$-heteroarylene; and n is selected from 0, 1, 2, 3, 4 and 5. Thus, $R^6$ may be a $C_1$–$C_{20}$ group selected from alkyl (e.g., alkyl and cycloalkyl, such as ethyl, propyl, butyl, hexyl, cyclohexyl, and adamantyl), heteroalkyl (e.g., $CH_3CH_2$—O-carbonyl, furanyl-carbonyl, hexyl-carbonyl, and adamantyl-carbonyl), aryl (e.g., phenyl and naphthyl), and heteroaryl (e.g., pyridyl). $R^7$ may be selected from alkylarylene (e.g., methylphenyl, ethylphenyl and cyclohexylphenyl), heteroalkylarylene (e.g., bromophenyl and methoxyphenyl), alkylheteroarylene (e.g., methylpyridyl), heteroalkylheteroarylene (e.g., methoxypyridyl), arylalkylene (e.g., phenylmethylene (ie., benzyl) and phenylethylene), heteroarylalkylene (e.g., pyridyl-$CH_2$—), arylheteroalkylene (e.g., phenylcarbonyl (i.e., benzoyl), naphthylcarbonyl, and phenyl-$CH_2CH_2$-carbonyl), heteroarylheteroalkylene (e.g., pyridyl-carbonyl), arylarylene (e.g., biphenyl), heteroarylarylene (e.g., pyridyl-phenyl), heteroarylheteroarylene (e.g., pyridyl—pyridyl), and arylheteroarylene (e.g., phenyl-pyridyl).

In addition, $R^6$ and $R^7$ may be selected from alkyl, heteroalkyl, aryl, heteroaryl, heterocycloalkyl, cycloalkylalkylene, arylalkylene, heteroarylalkylene, heterocycloalkylalkylene; alkyl-O, heteroalkyl-O, aryl-O, heteroaryl-O, cycloalkyl-O, heterocycloalkyl-O, cycloalkylalkylene-O, arylalkylene-O, heteroarylalkylene-O, heterocycloalkylalkylene-O; alkyl-CO, heteroalkyl-CO, aryl-CO, heteroaryl-CO, cycloalkyl-CO, heterocycloalkyl-CO, cycloalkylalkylene-CO, arylalkylene-CO, heteroarylalkylene-CO, heterocycloalkylalkylene-CO; alkyl-CONH, heteroalkyl-CONH, aryl-CONH, heteroaryl-CONH, cycloalkyl-CONH, heterocycloalkyl-CONH, cycloalkylalkylene-CONH, arylalkylene-CONH, heteroarylalkylene-CONH, heterocycloalkylalkylene-CONH; alkyl-OCO, heteroalkyl-OCO, aryl-OCO, heteroaryl-OCO, cycloalkyl-OCO, heterocycloalkyl-OCO, cycloalkylalkylene-OCO, arylalkylene-OCO, heteroarylalkylene-OCO, heterocycloalkylalkylene-OCO; alkyl-$SO_2$, heteroalkyl-$SO_2$, aryl-$SO_2$, heteroaryl-$SO_2$, cycloalkyl-$SO_2$, heterocycloalkyl-$SO_2$, cycloalkylalkylene-$SO_2$, arylalkylene-$SO_2$, heteroarylalkylene-$SO_2$, and heterocycloalkylalkylene-$SO_2$.

As mentioned previously, the term "independently at each occurrence" means that each selection is made independently of every other selection, so that no one selection impacts on any other selection, so long as a stable compound results. For instance, the selection of the atom at, for example, the "v" position is independent of the selection of the atom at any other position, that is, any of the w, x, y and z position, so long as a stable compound results. Thus, z and y may be C and C, or C and N, or N and C, or N and N, respectively. Independent of the selection of z and y, each of the positions v, w and x is filled with an atom selected from the group C, N, O and S.

The present inventors have discovered that compounds of biological activity result when each of the v, w, x, y and z positions is not filled with carbon. Thus, the compounds of the present invention have formula (1) such that each of w, v, x, y and z is not simultaneously C. In other words, the five-membered ring formed from positions v, w, x, y and z contains at least one heteroatom selected from N, O, and S.

The bond between each of two adjacent positions identified by v, w, x, y and z may be single or double, and again whether a bond is single or double at one location is independent of whether a bond is single or double at another location, so long as a stable structure results. A stable structure should be isolatable at room temperature. In a five-membered ring such as is formed by v, w, x, y and z, a double bond will be adjacent to two single bonds. Thus, the five membered ring formed from v, w, x, y and z may contain all single bonds, one double bond, or two double bonds. An oxygen will be bonded to two single bonds, a sulfur will be bonded to two single bonds, a carbon may be bonded to either two single bonds (in which case the carbon will also be bonded to two hydrogens to fulfill its open valence) or a double and a single bond (in which case the carbon will also be bonded to one hydrogen to fulfill its open valence), while a nitrogen will be bonded to either two single bonds (in which case the nitrogen will also be bonded to one hydrogen to fulfill its open valence) or a single and a double bond. In one aspect of the invention, the ring formed from v, w, x, y and z contains no unsaturation. In another aspect, the ring formed from v, w, x, y and z contains one site of unsaturation. In another aspect, the ring formed from v, w, x, y and z contains two sites of unsaturation.

In one aspect, the v, w, x, y and z positions are filled by four nitrogen atoms and, preferably, one carbon atom. For instance, the v, w, x, y, and z positions may be filled by N, N, N, N and C, respectively. As another example, the v, w, x, y, and z position may be filed by N, N, N, C, and N, respectively. Thus, in one aspect, the present invention provides a compound of the formula

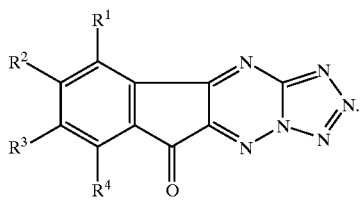

In another aspect, the present invention provides a compound of the formula

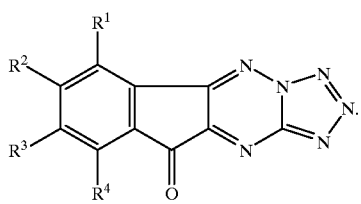

In one aspect, the v, w, x, y and z positions are filled by three nitrogen atoms and, preferably, two carbon atoms. For instance, the v, w, x, y, and z positions may be filled by N, C, N, N, and C, respectively. As another example, the v, w, x, y, and z position may be filed by N, C, N, C and N, respectively. Thus, in one aspect, the present invention provides a compound of the formula

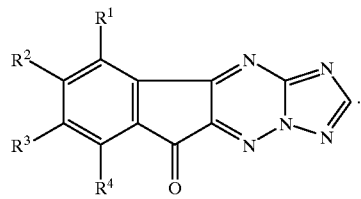

In another aspect, the present invention provides compounds of the formula

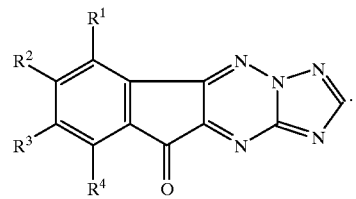

A convenient method of synthesizing compound of the present invention, as discussed in more detail below, combines a ninhydrin compound with a diamino compound. The reaction between the ninhydin and diamino compounds can, and typically does, result in two isomers. If the ninhydrin compound is unsymmetrically substituted, then additional regioisomers are possible. These isomers may, or may not, be separated to provide an efficacious compound of the present invention. Thus, in one aspect, the present invention provides a mixture of

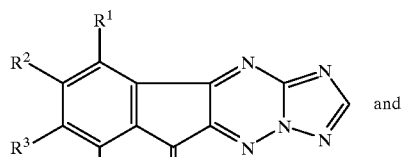

and

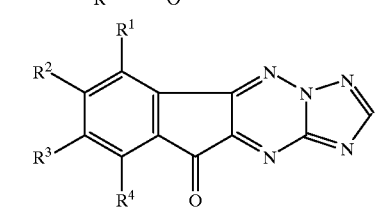

In another aspect, the present invention provides compounds wherein y and z are C, however each of v, w and x is not C. In one aspect, the positions v, w, and x are filled with N, O and S. For instance, the v, w, x, y, and z positions may be filled by N, O, N, C and C, respectively. As another example, the v, w, x, y and z positions may be filled by N, S, N, C and C, respectively. Thus, in one aspect, the present invention provides compounds of the formula

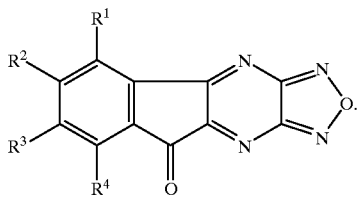

In another aspect, the present invention provides compounds of the formula

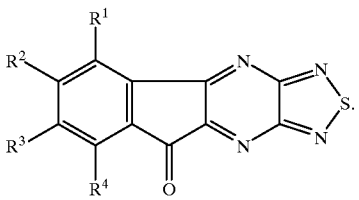

The compounds of the present invention may be prepared by combining a ninhydrin compound with a diamino compound as shown in the Scheme below.

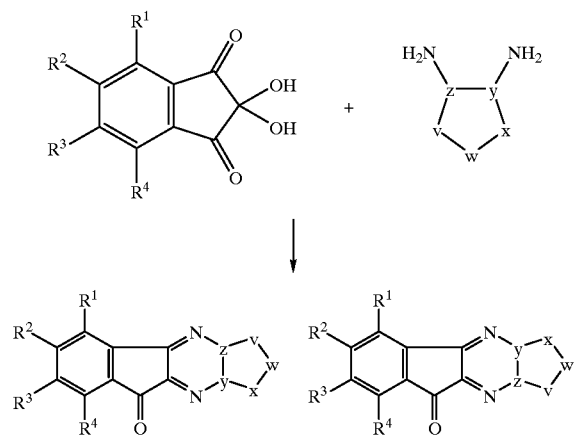

The two compounds are conveniently combined under acidic conditions, preferably at elevated temperature so as to enhance the rate of the reaction. Acidic conditions may be achieved by combining the ninhydrin compound with a protic acid, e.g., acetic acid, hydrochloric acid, phosphoric acid, sulfuric acid, hydrobromic acid, etc. Some water is also desirably present. The mixture of acid, water and ninhydrin compound is then heated, e.g., to about 60° C., and portions of diamino compound are added gradually. The addition of the diamino compound may be completed in ca. 5–10 minutes, when working on a 1–10 gram scale of each of ninhydrin and diamino compound. Alternatively, the diamino compound may be added in a single portion to the ninhydrin compound. Alternatively, the diamino compound may be added to the ninhydrin compound at room temperature.

Since the reaction product is the result of one molecule of ninhydrin compound reacting with one molecule of diamino compound, the ninhydrin and diamino compounds are preferably combined in approximately equimolar amounts. If a molar excess of either ninhydrin or diamino compound is used, the desired reaction product is still produced, however some unreacted starting material will be present at the end of the reaction. Purification of the desired product is made more difficult by the presence of greater amounts of unreacted starting material, and any by-products that may form therefrom.

After the ninhydrin and diamino compounds have been completely combined, the reaction temperature may be further increased in order to accelerate the rate of reaction between these two compounds. Conveniently, the reaction mixture is taken to the temperature at which the solvent refluxes. The mixture is held at reflux temperature for a sufficient period of time for the reaction to be completed, where this time is typically on the order of 10 minutes to 10 hours. The rate of the reaction will depend on the precise identity of the ninhydrin and diamino compounds, as well as the temperature of the reaction. The progress of the reaction may be monitored by thin layer chromatography.

As illustrated the Scheme above, the reaction between the ninhydrin and diamino compounds typically produces to isomeric products. Typically, these products are solids, and may not be soluble in water. Accordingly, at the conclusion of the reaction, the products may be isolated from liquid and water-soluble materials by filtration. Water may be used to wash the solid product, to thereby remove excess acid.

These products may be separated from one another, and also separated from any unreacted starting material(s) and any undesired by-products that may be contaminating the products, using standard separation techniques for mixtures organic chemicals, e.g., chromatography. For instance, the product mixture may be dissolved in a suitable organic solvent, e.g., choroform, ethanol, tetrahydrofuran, etc., and then eluted through a chromatography column, e.g., a silica gel-containing column. Capillary chromatography may be used to separate compounds that have similar chromatography retention times.

Suitable ninhydrin compounds and diamino compounds are well known to one of ordinary skill in the art, and may be synthesized by means well known to one of ordinary skill in the art and/or are commercially available chemicals. As used herein, "commercially available chemicals" and the chemicals used in the Examples set forth herein may be obtained from standard commercial sources including Acros Organics (Pittsburgh, Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.),Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire UK), Frontier Scientific (Logan, Utah), ICN Biomedicals, Inc. (Costa Mesa, Calif.), Key Organics (Cornwall U.K.), Lancaster Synthesis (Windham, N.H.), Maybridge Chemical Co. Ltd. (Cornwall U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hannover, Germany), Spectrum Quality Product, Inc. (New Brunswick, N.J.), TCI America (Portland Oreg.), Trans World Chemicals, Inc. (Rockville, Md.), and Wako Chemicals USA, Inc. (Richmond, Va.).

Reference books and treatise that detail the synthesis of reactants useful in the preparation of compounds of the present invention, or provide references to articles that describe the preparation, include, for example, "Synthetic Organic Chemistry", John Wiley & Sons, Inc., New York; S. R. Sandier et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-lnterscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., www.acs.org may be contacted for more details). Chemicals that are known but not commercially available in catalogs may be prepared by custom chemical synthesis houses, where many of the standard chemical supply houses (e.g., those listed above) provide custom synthesis services.

For example, ninhydrin itself is a commercially available material from, e.g., Aldrich (Milwaukee, Wis.; www.sigma-aldrich.com). Ninhydrin may undergo aromatic nucleophilic substitution reactions to provide substituted ninhydrin compounds. See, e.g., Della, E. W. et al., Synthesis (1999) 12:2119–2123 for specific examples of such reactions. Alternatively, 1-indanone and substituted derivatives thereof may be oxidized to the corresponding ninhydrin compound. See, e.g., Tatsugi, J.; and Izawa, Y., Synth. Commun. (1998) 28(5):859–864 for specific examples of oxidation conditions. 1-Indanone and substituted derivatives thereof are commercially available (see, e.g., Aldrich) or may be prepared by appropriate aromatic nucleophilic substitution reactions using commercially available indanone compounds as the starting material. Reaction conditions to achieve aromatic nucleophilic substitution reactions are well known to one of ordinary skill in the art. By these methods, ninhydrin compounds having suitable $R^1$, $R^2$, $R^3$ and $R^4$ groups are readily available. See, also, Venkov, A. P.; and Lukanov, L. K., Synth. Commun. (1996) 26(4):755–62; and Osadchii, S. A.; and Barkhash, V. A.; Zh. Org. Khim. (1970) 6(9):1815–20 for additional synthetic routes to substituted ninhydrin compounds. Joullie, M. M., et al., Tetrahedron, 47:8791–8830 (1991) provides a good review article on ninhydrin and ninhydrin analogs.

As used herein "suitable conditions" for carrying out a synthetic step are explicitly provided herein or may be discerned by reference to publications directed to methods used in synthetic organic chemistry. The reference books and treatise set forth above that detail the synthesis of reactants useful in the preparation of compounds of the present invention, will also provide suitable conditions for carrying out a synthetic step according to the present invention.

Likewise, diamino compounds suitable for preparing compounds of the present invention are very well known to one of ordinary skill in the art. Exemplary methods to prepare suitable diamino compounds are set forth below. The synthesis of 3,4-diaminofurazan is discussed in, e.g., Khimiya Gaterotsiklicheskikh Soiedinenji, No. 5, pp. 613–615, May, 1978 by A. V. Eremeev, et al. and references cited therein. See, e.g., Gaponik, P. N. et al, Khim Geoterotsikl. Soedin., 1683–6 (1984) for the synthesis of 1,5-diaminotetrazole from $HN_2NHC(=S)NH_2$ by treatment with $NaN_3/PbO/DMF$, boiling water, 6 hours.

The compounds of this invention can be incorporated into a variety of formulations for therapeutic administration. More particularly, the compounds of the present invention can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intracheal, etc., administration. The active agent may be systemic after administration or may be localized by the use of regional administration, intramural administration, or use of an implant that acts to retain the active dose at the site of implantation.

In pharmaceutical dosage forms, the compounds may be administered in the form of their pharmaceutically acceptable salts. They may also be used in appropriate association with other pharmaceutically active compounds. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional, additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like. Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres; slabs, etc. with biodegradable or non-biodegradable polymers. For example, polymers of lactic acid and/or glycolic acid form an erodible polymer that is well-tolerated by the host. The implant containing the inhibitory compounds may be placed in proximity to the site of a tumor, so that the local concentration of active agent is increased relative to the rest of the body.

The term "unit dosage form", as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to, be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

The combined use of the provided compounds of the present invention and other cytotoxic agents has the advantages that the required dosages for the individual drugs is lower, and the effect of the different drugs complementary. Depending on the patient and condition being treated and on the administration route, the subject compounds may be administered in dosages of 0.1 pg to 10 mg/kg body weight, per day. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage. Thus for example oral dosages in the rat maybe ten times the injection dose. Higher doses maybe used for localized routes of delivery.

A typical dosage may be a solution suitable for intravenous administration; a tablet taken from two to six times daily, or one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

For use in the subject methods, the subject compounds may be formulated with other pharmaceutically active agents, particularly other anti-metastatic, antitumor or anti-angiogenic agents. Angiostatic compounds of interest include angiostatin, endostatin, carboxy terminal peptides of collagen alpha (XV), etc. Cytotoxic and cytostatic agents of interest include adriamycin, alkeran, Ara-C, BICNU, busulfan, CNNU, cisplatinum, cytoxan, daunorubicin, DTIC, 5-FU, hydrea, ifosfamide, methotrexate, mithramycin, mitomycin, mitoxantrone, nitrogen mustard, velban, vincristine, vinblastine, VP-16, carboplatinum, fludarabine, gemcitabine, idarubicin, irinotecan, leustatin, navelbine, taxol, taxotere, topotecan, etc.

METHODS OF USE

The compounds of the invention have been shown to have anti-proliferative effect in an in vivo xenograft tumor model. The subject compounds are administered to a subject having a hyperproliferative disorders, e.g., to inhibit tumor growth, to decrease inflammation associated with a lymphoproliferative disorder, to inhibit graft rejection, or neurological damage due to tissue repair, etc.

The present compounds are useful for prophylactic or therapeutic purposes. As used herein, the term "treating" is used to refer to both prevention of disease, and treatment of pre-existing conditions. The prevention of proliferation is accomplished by administration of the subject' compounds prior to development of overt disease, e.g., to prevent the regrowth of tumors, prevent metastatic growth, diminish restenosis associated with cardiovascular surgery, etc. Alternatively the compounds are used to treat ongoing disease, by stabilizing or improving the clinical symptoms of the patient.

The host, or patient, may be from any mammalian species, e.g., primate sp., particularly humans; rodents, including mice, rats and hamsters; rabbits; equines, bovines, canines, felines; etc. Animal models are of interest for experimental investigations, providing a model for treatment of human disease.

The susceptibility of a particular cell to treatment with the subject compounds may be determined by in vitro testing. Typically a culture of the cell is combined with a subject compound at varying concentrations for a. period of time sufficient to allow the active agents to induce cell death or inhibit migration, usually between about one hour and one week. For in vitro testing, cultured cells from a biopsy sample may be used. The viable cells left after treatment are then counted.

The dose will vary depending on the specific compound utilized, specific disorder, patient status, etc. Typically a therapeutic dose will be sufficient to substantially decrease the undesirable cell population in the targeted tissue, while maintaining patient viability. Treatment will generally be continued until there is a substantial reduction, e.g., at least about 50%, decrease in the cell burden, and may be continued until there are essentially none of the undesirable cells detected in the body.

The compounds also find use in the specific inhibition of signaling pathway mediated by protein kinases. Protein kinases are involved in signaling pathways for such important cellular activities as responses to extracellular signals and cell cycle checkpoints. Inhibition of specific protein kinases provides a means of intervening in these signaling pathways, for example to block the effect of an extracellular signal, to release a cell from cell cycle checkpoint, etc. Defects in the activity of protein kinases are associated with a variety of pathological or clinical conditions, where there is a defect in signaling mediated by protein kinases. Such conditions include those associated with defects in cell cycle regulation or in response to extracellular signals, e.g., hyperglycemia and diabetes Type I and Type II, immunological disorders, e.g., autoimmune and immunodeficiency diseases; hyperproliferative disorders, which may include psoriasis, arthritis, inflammation, endometriosis, scarring, cancer, etc.

The compounds of the present invention are active in inhibiting purified kinase proteins, i.e., there is a decrease in the phosphorylation of a specific substrate in the presence of the compound. The compounds of the invention may also be useful as reagents for studying signal transduction or any of the clinical disorders listed throughout this application.

HYPERPROLIFERATIVE DISORDERS

There are many disorders associated with a dysregulation of cellular proliferation. The conditions of interest include, but are not limited to, the following conditions.

The subject compounds are useful in the treatment of a variety of conditions where there is proliferation and/or migration of smooth muscle cells, and/or inflammatory cells into the intimal layer of a vessel, resulting in restricted blood flow through that vessel, i.e., neointimal occlusive lesions. Occlusive vascular conditions of interest include atherosclerosis, graft coronary vascular disease after transplantation, vein graft stenosis, peri-anastomatic prosthetic graft stenosis, restenosis after angioplasty or stent placement, and the like.

Diseases where there is hyperproliferation and tissue remodelling or repair of reproductive tissue, e.g., uterine, testicular and ovarian carcinomas, endometriosis, squamous and glandular epithelial carcinomas of the cervix, etc. are reduced in cell number by administration of the subject compounds. The growth and proliferation of neural cells is also of interest.

Tumor cells are characterized by uncontrolled growth, invasion to surrounding tissues, and metastatic spread to distant sites. Growth and expansion requires an ability not only to proliferate, but also to down-modulate cell death (apoptosis) and activate angiogenesis to produce a tumor neovasculature.

Tumors of interest for treatment include carcinomas, e.g., colon, duodenal, prostate, breast, melanoma, ductal, hepatic, pancreatic, renal, endometrial, stomach, dysplastic oral mucosa, polyposis, invasive oral cancer, non-small cell lung carcinoma, transitional and squamous cell urinary carcinoma etc.; neurological malignancies; e.g., neuroblastoma, gliomas, etc.; hematological malignancies, e.g., childhood acute leukaemia, non-Hodgkin's lymphomas, chronic lymphocytic leukaemia, malignant cutaneous T-cells, mycosis fungoides, non-MF cutaneous T-cell—lymphoma, lymphomatoid papulosis, T-cell rich cutaneous lymphoid hyperplasia, bullous pemphigoid, discoid lupus erythematosus, lichen planus, etc.; and the like.

Tumors of neural tissue are of particular interest, e.g., gliomas, neuromas, etc. Some cancers of particular interest include breast cancers, which are primarily adenocarcinoma subtypes. Ductal carcinoma in situ is the most common type of noninvasive breast cancer. In DCIS, the malignant cells have not metastasized through the walls of the ducts into the fatty tissue of the breast. Infiltrating (or invasive) ductal carcinoma (IDC) has metastasized through the wall of the duct and invaded the fatty tissue of the breast. Infiltrating (or invasive) lobular carcinoma (ILC) is similar to IDC, in that it has the potential metastasize elsewhere in the body. About 10% to 15% of invasive breast cancers are invasive lobular carcinomas.

Also of interest is non-small cell lung carcinoma. Non-small cell lung cancer (NSCLC) is made up of three general subtypes of lung cancer. Epidermoid carcinoma (also called squamous cell carcinoma) usually starts in one of the larger bronchial tubes and grows relatively slowly. The size of these tumors can range from very small to quite large. Adenocarcinoma starts growing near the outside surface of the lung and may vary in both size and growth rate. Some slowly growing adenocarcinomas are described as alveolar cell cancer. Large cell carcinoma starts near the surface of the lung, grows rapidly, and the growth is usually fairly large when diagnosed. Other less common forms of lung cancer are carcinoid, cylindroma, mucoepidermoid, and malignant mesothelioma.

Melanoma is a malignant tumor of melanocytes. Although most melanomas arise in the skin, they also may arise from mucosal surfaces or at other sites to which neural crest cells migrate. Melanoma occurs predominantly in adults, and more than half of the cases arise in apparently normal areas of the skin. Prognosis is affected by clinical and histological factors and by anatomic location of the lesion. Thickness and/or level of invasion of the melanoma, mitotic index, tumor infiltrating lymphocytes, and ulceration or bleeding at the primary site affect the prognosis. Clinical staging is based on whether the tumor has spread to regional lymph nodes or distant sites. For disease clinically confined to the primary site, the greater the thickness and depth of local invasion of the melanoma, the higher the chance of lymph node metastases and the worse the prognosis. Melanoma can spread by local extension (through lymphatics) and/or by hematogenous routes to distant sites. Any organ may be involved by metastases, but lungs and liver are common sites.

Other hyperproliferative diseases of interest relate to epidermal hyperproliferation, tissue, remodeling and repair. For example, the chronic skin inflammation of psoriasis is associated with hyperplastic epidermal keratinocytes as well as infiltrating mononuclear cells, including CD4+ memory T cells, neutrophils and macrophages.

The proliferation of immune cells is associated with a number of autoimmune and lymphoproliferative disorders. Diseases of interest include multiple sclerosis, rheumatoid arthritis and insulin dependent diabetes mellitus. Evidence suggests that abnormalities in apoptosis play a part in the pathogenesis of systemic lupus erythematosus (SLE). Other lymphoproliferative conditions the inherited disorder of lymphocyte apoptosis, which is an autoimmune lymphoproliferative syndrome, as well as a number of leukemias and lymphomas. Symptoms of allergies to environmental and food agents, as well as inflammatory bowel disease, may also be alleviated by the compounds of the invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g., amounts, temperature, concentration, etc.) but some experimental errors and deviations should be allowed for. Unless otherwise indicated, the reactants and reagents used in the following specific examples were analytical grade or better and were used without further purification. Compounds (including starting materials) that are not commercially available can be prepared by employing known methods from the chemical literature, including methods set forth in the references identified above.

EXAMPLES

Example 1

Synthesis of 1,5-diaminotetrazole

To a round bottom flask equipped with a condenser and a stirring bar, purged with $N_{2(g)}$ was charged with thiosemicarbazide (18.3 g, 0.20 moles), and sodium azide (16.3 g, 0.25 moles). Anhydrous N,N-dimethylformamide (350 mL) was then added to it. Lead (II) oxide (89.3 g, 0.40 moles) was slowly added to the flask with stirring. A black suspension was obtained. The solution was heated to 100° C. and kept stirring for 6 hours. The solution was filtered through a celite cake while hot resulting in a colorless transparent solution. The solvent was removed using a rotary evaporator and the greyish residue obtained was dissolved in 50 mL of boiling water. The solution was filtered while hot and the filtrate was slowly cooled to 4° C. A white crystalline solid was precipitated. The solid was collected by filtration and dried under high vacuum. White cube crystals were isolated (6.0 g, 30%), m.p.=186–187° C. FTIR (KBr pellet, cm$^{-1}$) 3325 (s), 3150 (s), 1655 (s), 1576 (s), 1486 (m), 1329 (s), 1135 (m), 1109 (s), 1077 (s), 1002 (s), 932 (s), 789 (m), 746 (m), 684 (s), 605 (s).

Example 2

Synthesis of 3,4-diamino-1,2,4-triazole 1,3-Diaminoguanidine (2.03 g, 22.7 mmol) was pulverized using a pestle and mortar until a fine white powder was obtained. This white powder was suspended in 30 mL of 1,4-dioxane (0.75 M) in a round bottom flask equipped with a stirring bar and a condenser. One equivalent of formic acid (1 mL) was added and the solution was heated to 102° C. while stirring for 16 hours. The solution was cooled to room temperature slowly and the yellow precipitate was isolated by filtration and dried under high vacuum. The dry product was then recrystallized from minimal amounts of boiling ethanol and the final product was faint yellow needle crystals (1.65 g, 59%).

Example 3

Synthesis of 3,4-diamino-1,2,5-thiadiazole

Potassium phthalimide (2.47 g) was weighed into a dry round bottom flask, the salt was then dried under high vacuum for one hour. The Flask was then purged with argon gas for ten minutes. The phthalimide was then dissolved in 15 mL of anhydrous DMF, the solution was heated to 100° C. with stirring. 3,4-Dichloro-1,2,5-thiadiazole (1.1 g) was then added slowly to the reaction vessel. The solution was then stirred for 20 minutes at 100° C. The reaction mixture was then cooled to room temperature over one hour while stirring. The DMF solution was then poured over water at room temperature with stirring, an orange granular precipitate then formed. The precipitate was collected by filtration and dried for two hours under high vacuum. This solid was then dissolved in a 50:50 acetone:chloroform mixture and the resulting solution was decolorized with charcoal and white needle-like crystals were obtained (0.53 g, yield 20%). 3,4-Di-(N-phthaloyl)-1,2,5-thiadiazole (230 mg) was then dissolved in 7 mL of DMF and cooled to 0° C. in an ice bath with stirring. Ammonia gas was bubbled through the solution for ten minutes. The solution was then stirred at room temperature for another hour. The excess ammonia gas was removed from the DMF via an aspirator. The DMF was then removed via vacuum distillation, and a light yellow precipitate remained. The by-product phthalimide was removed by dissolving the precipitate in an ethanol water mixture. The yellow crystals were discarded and the filtrate was then dried and the light yellow precipitate that remained was suspended in 4 mL of water. The presence of the desired product was confirmed by tlc analysis.

Example 4

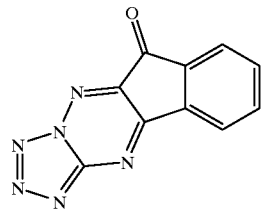

4A

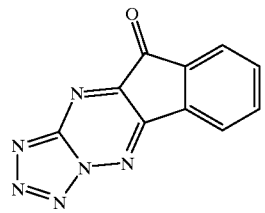

4B

In a 250 mL round-bottom flask, equipped with a condenser and magnetic stir bar, was placed ninhydrin (5.9 g, 33 mmol), concentrated hydrochloric acid (0.3 mL) and water (70 mL). This solution was warmed up to 60° C. with stirring. 1,5-Diaminotetrazole (3.0 g, 30 mmol) was added in small portions over 5 min. The solution was then heated to reflux for 30 min and cooled. The crude product was collected on a funnel and washed with water (5.56 g, 83%). The crude product (600 mg) was purified by chromatography on silica gel eluting with chloroform/ethanol (98:2) to give a light yellow powder (550 mg). TLC analysis (ethyl acetate/hexanes 1:1) and NMR spectra indicated that the product consisted of 4A and 4B with a ratio of about 1:1. $^1$H NMR (DMSO-d$_6$, ppm, mixture of two isomers): 8.35 (m, 1H), 8.2-7.9 (m, 3H). $^{13}$C NMR (DMSO-d$_6$, ppm, mixture of two isomers) 123.99, 124.64, 125.21, 125.34, 135.29, 136.10, 136.32, 137.89, 138.28, 138.33, 138.71, 139.49, 148.91, 149.56, 149.85, 153.83, 157.92, 162.50, 183.13, 184.16. Mass spectrum (EI, m/z): 224 (M$^+$), 196, 168, 140, 88 (100%).

Example 5

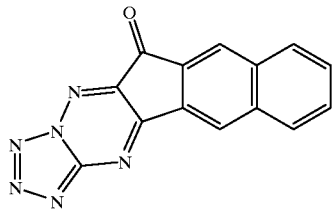

5A

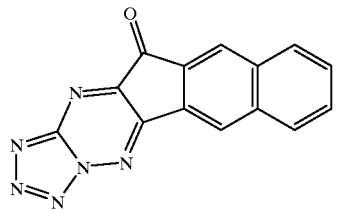

5B

+In a round-bottom flask, equipped with a condenser and magnetic stir bar, was placed benzo[f]ninhydrin (25 mg, 0.11 mmol), concentrated hydrochloric acid (0.036 mL) and water (1 mL). This suspension was warmed up to 60° C. with stirring. 1,5-Diaminotetrazole (12 mg, 0.12 mmol) was added in one portion. The mixture was then heated to reflux for 9 h and then cooled. The crude product was collected on a funnel and washed with water (9 mg, orange powder). TLC analysis (ethyl acetate/hexanes 1:1) indicates that the product consist of two isomers with a ratio of about 1:1 (2 and 3). $^1$H NMR (200 MHz, CDCl$_3$): indicating a mixture of two isomers.

Example 6

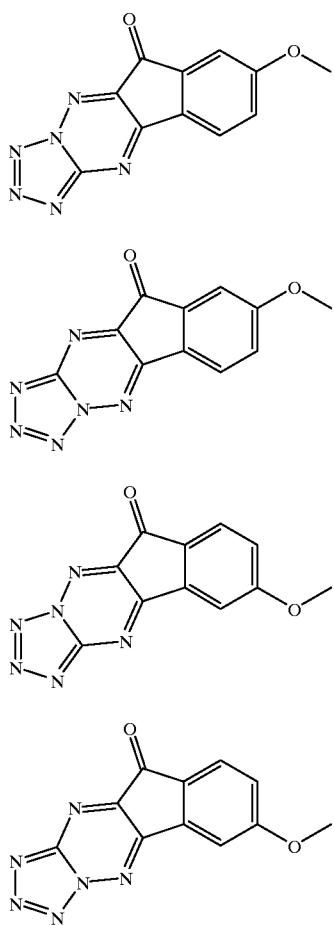

In a round-bottom flask, equipped with a condenser and magnetic stir bar, was placed 5-methylninhydrin (30 mg, 0.14 mmol), concentrated hydrochloric acid (one drop) and water (1 mL). This suspension was warmed up to 60° C. with stirring. 1,5-Diaminotetrazole (22 mg, 0.22 mmol) was added in one portion. The solution was then heated to reflux for 6 h and then cooled. The crude product was collected on a funnel and washed with water (18 mg, red powder). TLC analysis (ethyl acetate/hexanes 1:1) and $^1$H NMR indicate that the product consist of two of the four isomers drawn above, with a ratio of about 1:1. $^1$H NMR (CDCl$_3$, ppm): mixture of two isomers 8.37.3 (m, 3H), 4.15, 4.05 (two singlets, 3H).

Example 7

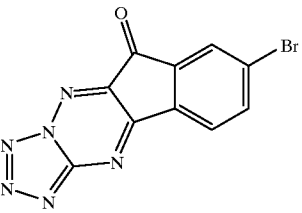

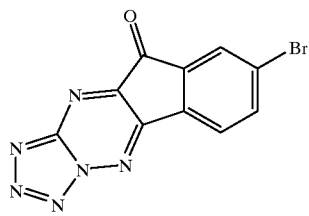

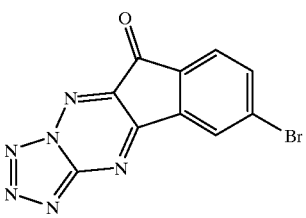

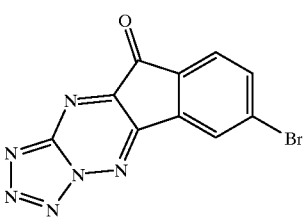

To a solution of 6-bromo-1-indanone (277 mg, 1.26 mmol) in 6.3 mL of DMSO was added NBS (225.0 mg, 1.26 mmol) in one portion while stirring at 40° C. The resulting transparent blood red solution was stirred for another two hours at this temperature. The temperature was then elevated to 80° C. and the pressure was reduced using an aspirator. The reaction was continued under these conditions for an additional 6 hours. The solution was then cooled to room temperature, at which point it was poured into 400 mL of water and extracted with 3×25 mL of dichloromethane. The aqueous layer was saturated with sodium chloride and extracted with 5×25 mL of ethyl acetate. The ethyl acetate layer was dried with Na$_2$SO$_4$, filtered, and evaporated to dryness. The crude material was purified by flash chromatography on silica gel, eluting with ethyl acetate:hexanes (5:1) to afford the product, a mixture of 6-bromoninhydrin regio isomers, in a yield of 45%, as an off white solid.

A mixture of two or more of the compounds 7A, 7B, 7C and 7D, obtained as a deep yellow powder, was synthesized using 1,5-diaminotetrazole (70.0 mg, 0.7 mmol) and 6-bromoninhydrin (164 mg, 0.63 mmol) obtained above, in a yield of 39%, after purification by chromatography on silica gel eluting with hexane:ethyl acetate 5:1.

Example 8

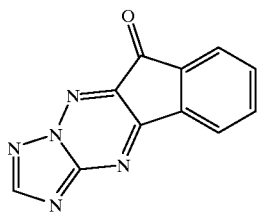

8A

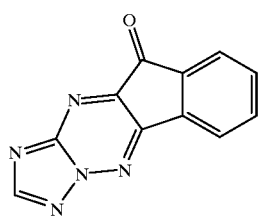

8B

One or both of these compounds, obtained as a yellow powder, was synthesized using 3,4-diamino-1,2,4-triazole (1.35 g, 13.6 mmol) and ninhydrin (2.43 g, 13.6 mmol), in a yield of 58%. $^1$H NMR (ppm, DMSO-D$_6$): 7.8–8.4 (m, 4H), 9.8 (s, 1H); MS (EI, m/z): 225 (14%) (M+2), 224 (100%) (M+1), 100 (22%).

Example 9

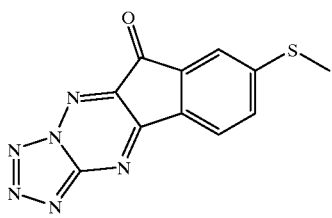

9A

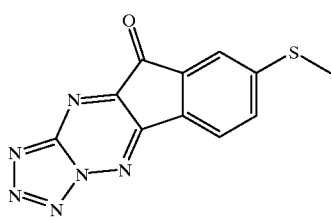

9B

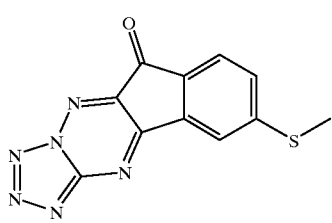

9C

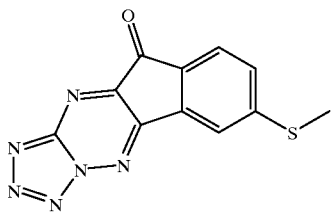

9D

To a solution of 6-(methylthio)indanone (1.0 g, 5.61 mmol) in carbon tetrachloride (40 mL) was added NBS (3.0 g, 16.9 mmol) and AIBN (30 mg) at room temperature. The mixture was heated to reflux, while being illuminated with a 100 W light. After 4.5 h the mixture was cooled to 0° C. and filtered. The resulting solid was washed with CCl$_4$. At room temperature triethylamine (2.75 ml, 19.6 mmol) was added to the filtrate, and the reaction mixture was allowed to stir for one hour. A solid was removed by filtration and washed with CCl$_4$. The filtrate was washed with 1 N HCl, 5% NaHCO$_3$, then water, dried over Na$_2$SO$_4$, filtered, and concentrated under reduced pressure to afford an oil/solid mixture (1.36 g). This material was used in the next step without further purification.

The crude material (1.36 g) was dissolved in benzene (20 mL and 20 mL of DMSO was added, followed by the addition of bromine (0.2 mL). This deep red solution was heated under reflux for 5 h, at which point, it was allowed to cool to room temperature and stirred overnight. Water (40 ml) was added to the reaction solution and the mixture was extracted with ethyl acetate. The organic layer was dried with Na$_2$SO$_4$, filtered, and evaporated to dryness under reduced pressure. The resulting crude material was purified by flash chromatography on silica gel eluting with first hexane:CH$_2$Cl$_2$, and then hexane:EtOAc, to yield 0.452 g (36%) of pure 2,2-dihydroxy-6-(methylthio)ninhydrin. See also, Heffner, R. J. and Joullie, M. M., *Synthetic Communications,* 21(21):2231–2256 (1991) for further discussion of these compounds.

A mixture of two or more of the compounds 9A, 9B, 9C and 9D, obtained as a yellow powder, was synthesized using, 1,5-diaminotetrazole (0.35 g, 1.65 mmol) and 2,2-dihydroxy-6-(methylthio)ninhydrin (0.336 g, 1.63 mmol) obtained above, in a 27% yield, after purification by chromatography, on silica gel eluting with ethyl acetate:hexanes (1:1).

Example 10

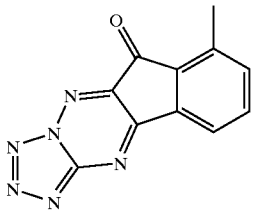

10A

10B

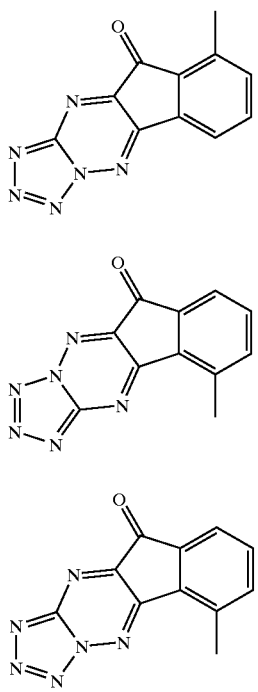

10C

10D

A mixture including one or more of the isomer shown above, obtained as a yellow powder, was synthesized using 1,5-diaminotetrazole (0.59 g, 5.9 mmol) and 4-methylninhydrin (0.54 g, 2.8 mmol) which was obtained by oxidation of 4-methyl-1-indanone with NBS, in a yield of 21%.

Example 11

11A

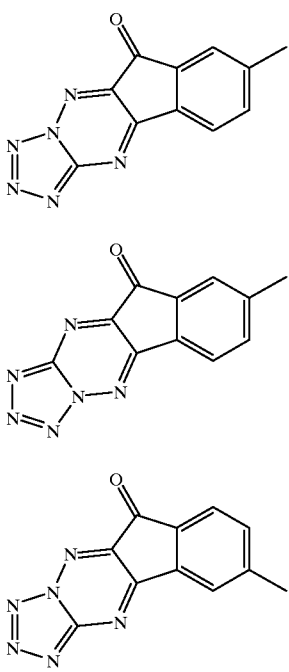

11B

11C

11D

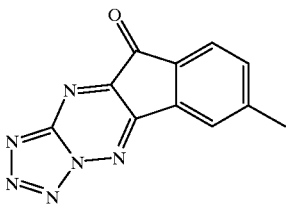

6-Methyl-1-indanone (2.50 g, 17.0 mmol) was dissolved in DMSO (80 mL, 0.23 M) in a round bottom flask equipped with a stirring bar. While stirring this solution was heated to 40° C. and NBS (6.12 g, 34.0 mmol) was added in a single portion, resulting in a blood red homogenous solution. This resulting solution was stirred at 40° C. for 2 hours at atmospheric pressure. Using a water aspirator the pressure of the reaction vessel was decreased and the temperature was increased to 80° C. This was then stirred for an additional 6 hours, resulting in a red homogeneous solution. This solution was cooled to room temperature and poured over 400 mL of water while stirring, resulting in a yellow opaque solution. The aqueous layer was washed with 5×25 mL of $CH_2Cl_2$, then saturated with sodium chloride and extracted with ethyl acetate (8×30 mL). The organic phase was dried with anhydrous sodium sulphate and the ethyl acetate was removed using a rotary evaporator, to dryness yielding a light green transparent oil. This was further purified by dissolving the oil in minimal amounts of $CH_2Cl_2$ and eluting through a $SiO_2$ column with a 10:1 ($CH_2Cl_2$:MeOH) solvent system, yielding a yellow transparent oil (2.0 g, 61%).

One or more of the isomer drawn above, obtained as a yellow powder, was synthesized using 1,5-diaminotetrazole (0.54 g, 5.4 mmol) and 5-methylninhydrin (0.5 g, 2.6 mmol) obtained above, in a yield of 22% $^1$H NMR (ppm, DMSO-$d_6$): 2.6 (s, 3H), 7.8–8.3 (m, 3H); MS (m/z): 240 (14%) (M+2), 239 (100%) (M+1), 183 (22%), 100. FTIR (KBr pellet, cm$^{-1}$): 627(w), 661(w), 668(w), 736(m), 766(m), 798 (m), 823(m), 965(m), 1068(m), 1204(s), 1240(m), 1270(m), 1309(m), 1379(m), 1484(m), 1511(s); 1595(s); 1613(s), 1734(vs), 2925(w).

Example 12

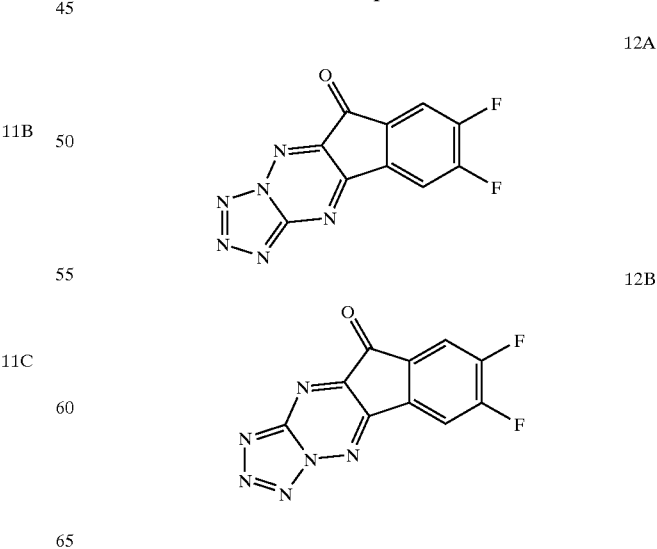

This compound, obtained as a yellow powder, was synthesized using 1,5-diaminotetrazole (55 mg, 0.56 mmol) and 5,6-difluoroninhydrin (60 mg, 0.2 mmol) which was obtained by oxidation of 5,6-difluoro-1-indanone with NBS, in a yield of 14%, after purification by chromatography on silica gel eluting with ethyl acetate. $^1$H NMR (ppm, DMSO-$d_6$): 8.4 (t, 1 H), 8.6 (t,1 H).

Example 13

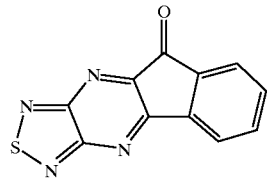

This compound, obtained as a yellow powder, was synthesized using 3,4-diamino-1,2,5-thiadiazole (70 mg, 0.76 mmol) and ninhydrin (0.28 g, 1.59 mmol), in a yield of 46%, after purification by chromatography on silica gel eluting with ethyl acetate. $^1$H NMR (ppm, DMSO-$d_6$): 7.9 (d, 1H), 8.0 (t, 2H), 8.2 (d, 1H); MS (m/z) 241 (19%) (M+2), 241 (100%) (M+1), 240 (91%) (M), 212 (6%), 188 (9%), 160 (13%), 79 (7%). FTIR (KBr pellet, cm$^{-1}$): 624 (m), 638 (m), 710 (m), 745 (s), 767 (m), 814 (m), 882 (s), 934 (m), 1054 (m), 1157 (m), 1193 (s), 1226 (s), 1252 (s), 1291 (m), 1303 (m), 1334 (w), 1382 (m), 1474 (m), 1578 (vs), 1603 (m), 1722 (vs), 3014 (m), 3079 (m).

Example 14

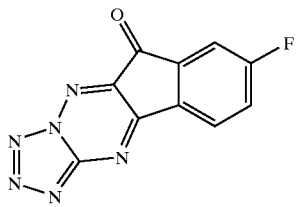
14A

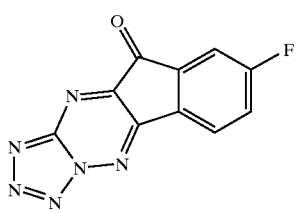
14B

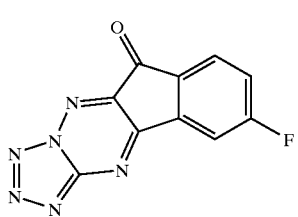
14C

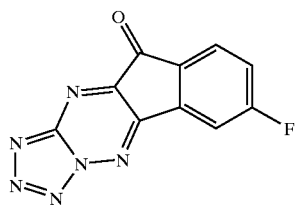
14D

To a solution of 5-fluoroindanone (150 mg, 1.0 mmol) in dimethylsulfoxide (4.0 mL) was added NBS (178 mg, 2 mmol) in one potion at 40° C. The mixture was stirred for 4 hours at the same temperature and then heated at 80° C. under aspirator for 2 h. The hot mixture was poured into water (20 mL) and extracted with methylene chloride. The first extraction was discarded and the rest of extraction was combined. Removal of solvent yielded a brown liquid. The liquid was purified by column chromatography (eluent methylene/ethyl estate) and a brown liquid was obtained (191 mg). A mixture of ether and hexanes was added to the liquid and a precipitate was formed. The precipitate was removed by filtration. Yellow oil (78 mg) was obtained after removal of solvents.

To the solution of the above yellow oil (78 mg) in hot water were added conc. HCl (2 drops) and 1,5-diaminotetrazole (40 mg) and the mixture was stirred for 6 hour at 80° C. The reaction mixture was allowed to cool and the product was collected by filtration and washed with water. Chromatography (silica gel, 70–230 meshes, EtOAc) purification afforded the product as a yellow powder (41 mg, total yield 53%).

Example 15

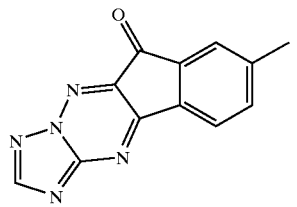
15A

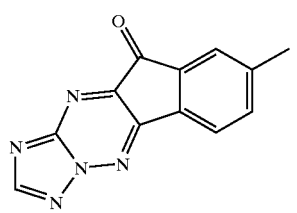
15B

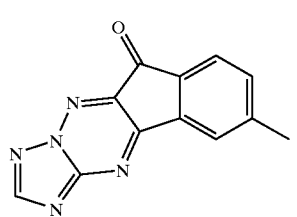
15C

-continued

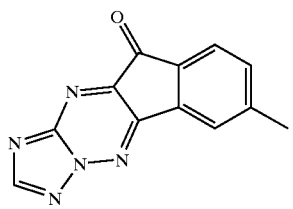

15D

To a round bottom flask equipped with a stirring bar containing 6-methyininhydrin (2.0 g, 10.4 mmol) was added 180 mL of water. The resulting solution was heated to 90° C. while stirring and catalytic amounts of hydrochloric acid were added (1–2 mL), resulting a transparent yellow solution. To this solution 1,5-diaminotetrazole (1.55 g, 15.60 mmol) was added in a single portion and the mixture was kept stirring for one hour. The heat was then removed and stirring was continued at room temperature for 16 hours. The yellowish orange precipitate was collected and dried under high vacuum. The dry solid was dissolved in ethyl acetate (1 L/g) and eluted through a silica gel plug (15×2 cm/g). The first yellow fraction was collected. The solvent was removed using a rotary evaporator and dried under high vacuum, yielding a bright yellow solid (1.77 g, 48%). MS (ES+, m/z): 238 [M]$^+$; $^1$H NMR (DMSO-d$_6$, ppm): 2.5 (s, 3H), 8.0 (m, 3H), 9.7 (s, 1H).

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:
1. A compound of the formula

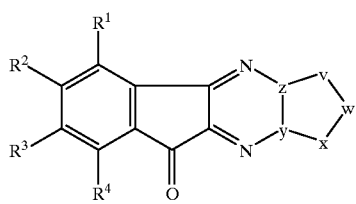

wherein, independently at each occurrence,
- v, w, and x are selected from C, N, O, and S, with H substitution as needed to fulfill open valence sites;
- y and z are selected from N and C, with H substitution as needed to fulfill open valence sites, with the proviso that each of w, v, x, y and z is not simultaneously C;
- the ring formed from v, w, x, y and z may be saturated or unsaturated; and
- R$^1$, R$^2$, R$^3$ and R$^4$ are selected from hydrogen, alkyl, aryl, alkaryl, aralkyl, heteroalkyl, and heteroaryl; wherein any adjacent two of R$^1$, R$^2$, R$^3$ and R$^4$ may join together with the carbon atoms they are attached to, to form a 5, 6 or 7-membered carbocyclic ring or a 5, 6 or 7-membered heterocyclic ring containing at least one atom selected from nitrogen, oxygen and sulfur, with the proviso that each of R$^1$, R$^2$, R$^3$ and R$^4$ is not simultaneously hydrogen.

2. A compound of claim 1 having a formula selected from

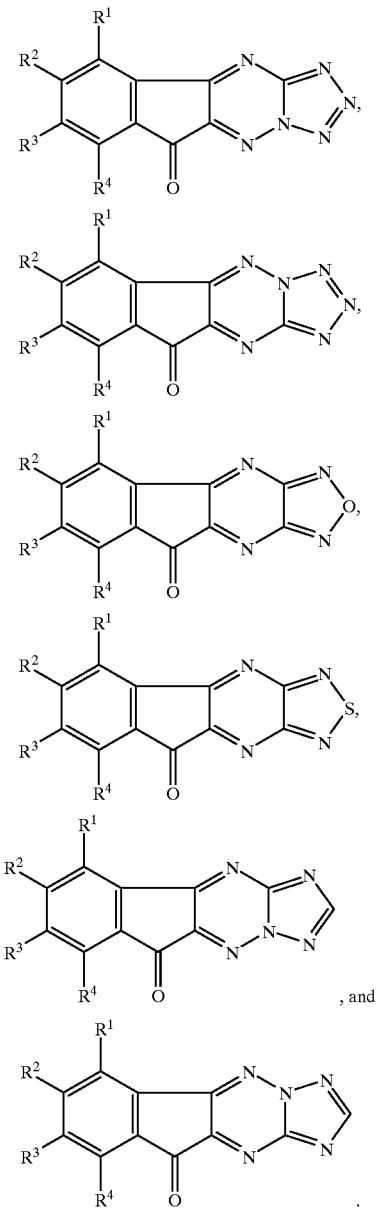

, and

3. A compound of claim 1 wherein at least one of R$^1$, R$^2$, R$^3$ and R$^4$ is a heteroalkyl group selected from groups of the formula R$^5$—O— and R$^5$—S— wherein R$^5$ is C$_1$–C$_{15}$ hydrocarbyl or heteroalkyl.

4. A compound of claim 3 wherein R$^5$ is C$_1$–C$_6$ hydrocarbyl.

5. A compound of claim 1 having a formula selected from

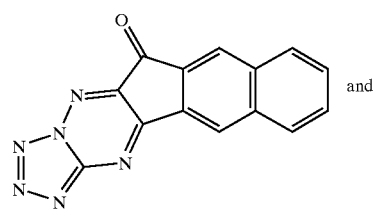

and

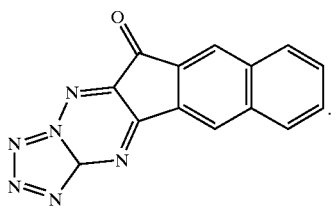
6. A compound of claim 1 having a formula selected from
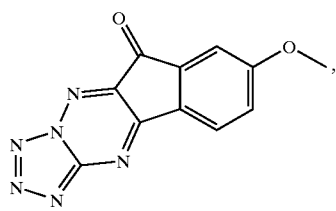
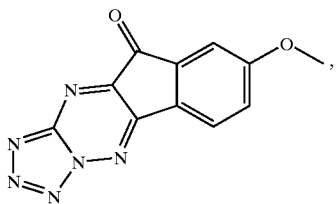
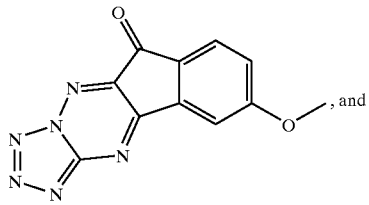
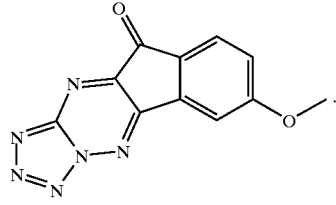
7. A compound of claim 1 having a formula selected from
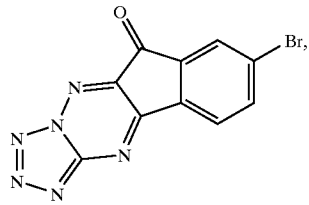
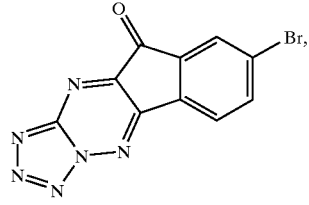
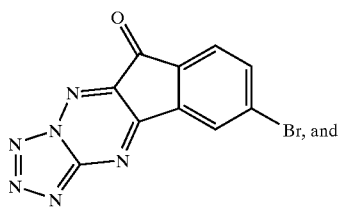
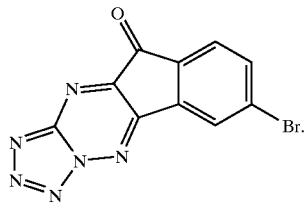
8. A compound of claim 1 having a formula selected from
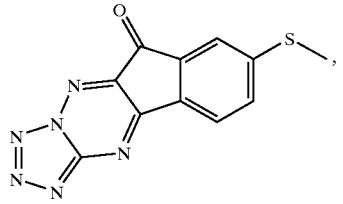
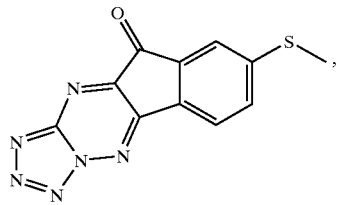
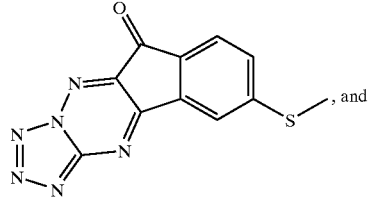
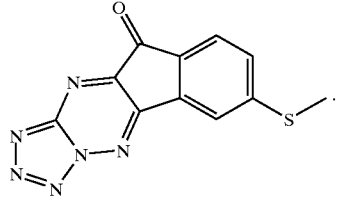
9. A compound of claim 1 having a formula selected from
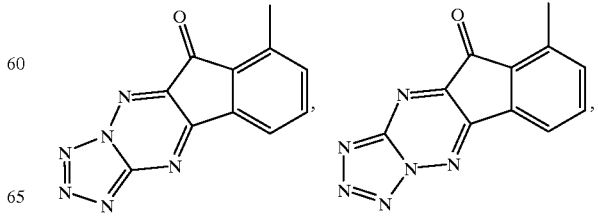

-continued
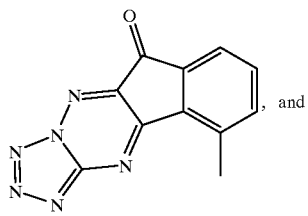, and
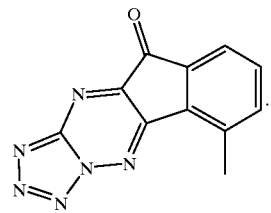.
10. A compound of claim 1 having a formula selected from
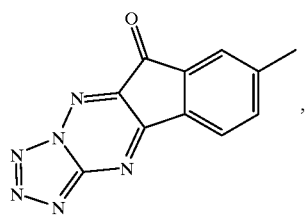,
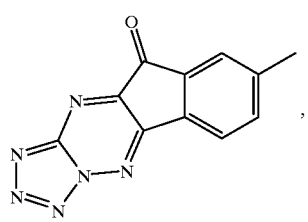,
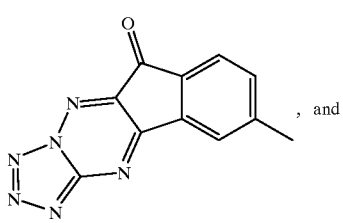, and
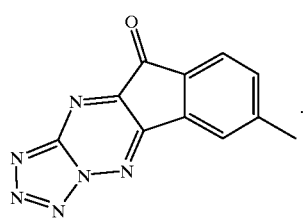.
11. A compound of claim 1 having a formula selected from
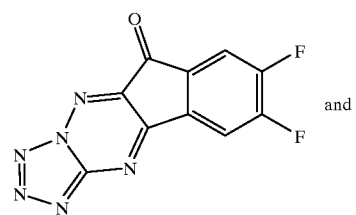, and
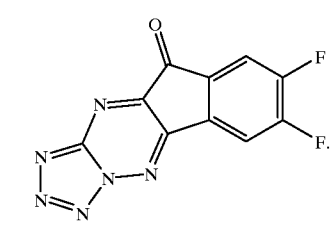.
12. A compound of claim 1 having a formula selected from
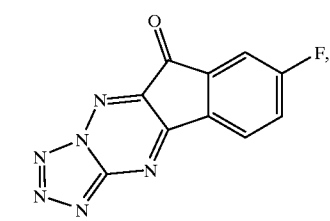,
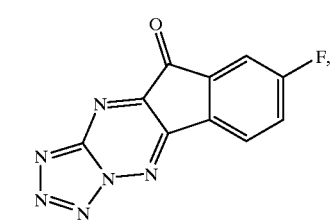,
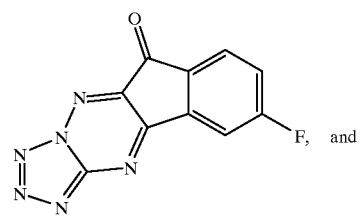, and
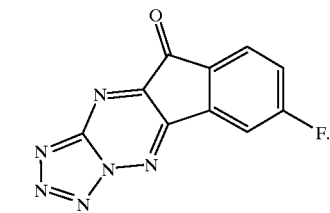.
13. A compound of claim 1 having a formula selected from

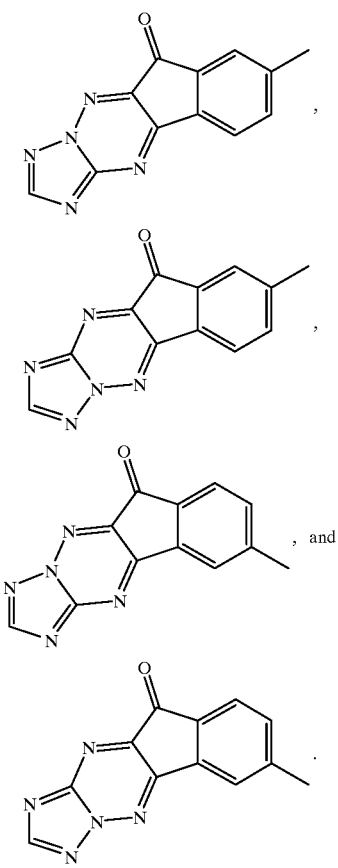

,

, and

.

14. A compound of claim 1 wherein at least one of $R^1$, $R^2$, $R^3$ and $R^4$ is a heteroalkyl group selected from fluorine, chlorine, bromine and iodine.

15. A compound of claim 1 wherein $R^2$ and $R^3$ join together to form a compound as shown in the formula

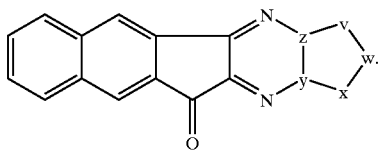

16. A compound of claim 1 wherein at least one of $R^1$, $R^2$, $R^3$ and $R^4$ is an alkyl group selected from $C_1$–$C_{15}$ alkyl.

17. A compound of claim 1 wherein at least one of $R^1$, $R^2$, $R^3$ and $R^4$ is an alkyl group selected from $C_1$–$C_6$ alkyl.

18. A pharmaceutical composition comprising a pharmaceutically acceptable carrier, excipient or diluent, and a compound of the formula

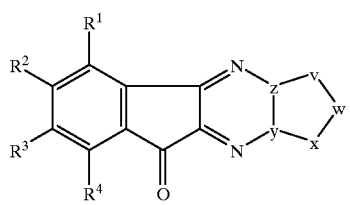

wherein, independently at each occurrence, v, w, and x are selected from C, N, O, and S, with H substitution as needed to fulfill open valence sites;

y and z are selected from N and C, with H substitution as needed to fulfill open valence sites, with the proviso that each of w, v, x, y and z is not simultaneously C;

the ring formed from v, w, x, y and z may be saturated or unsaturated; and $R^1$, $R^2$, $R^3$ and $R^4$ are selected from hydrogen, alkyl, aryl, alkaryl, aralkyl, heteroalkyl, and heteroaryl; wherein any adjacent two of $R^1$, $R^2$, $R^3$ and $R^4$ may join together to form a 5, 6 or 7-membered carbocyclic ring or a 5, 6 or 7-membered heterocyclic ring containing at least one atom selected from nitrogen, oxygen and sulfur.

19. A composition of claim 18, with the proviso that each of $R^1$, $R^2$, $R^3$ and $R^4$ is not simultaneously hydrogen.

20. A composition of claim 18 comprising a compound having a formula selected from

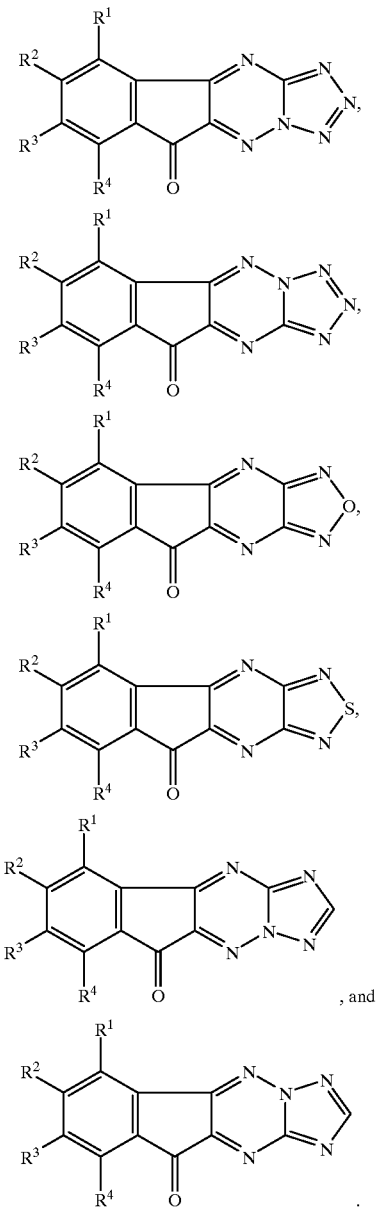

, and

.

21. A composition of claim 18 wherein at least one of $R^1$, $R^2$, $R^3$ and $R^4$ is a heteroalkyl group selected from groups of the formula $R^5$—O— and $R^5$—S— wherein $R^5$ is $C_1$–$C_{15}$ hydrocarbyl or heteroalkyl.

22. A composition of claim 18 wherein $R^5$ is $C_1$–$C_6$ hydrocarbyl.

23. A composition of claim 18 comprising a compound having a formula selected from

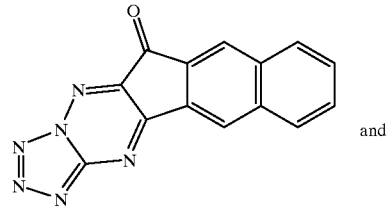

and

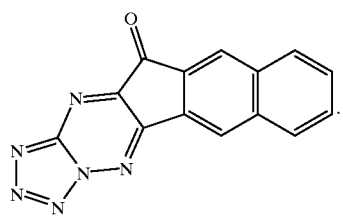

24. A composition of claim 18 comprising a compound having a formula selected from

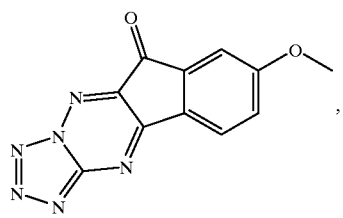

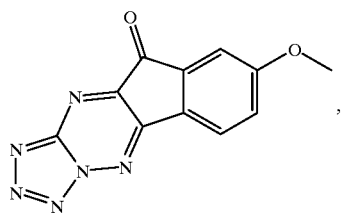

, and

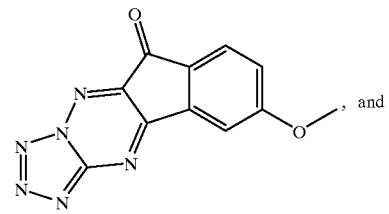

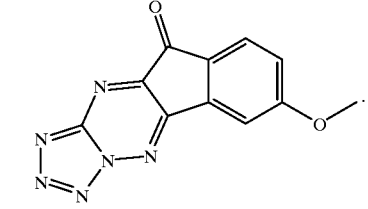

25. A composition of claim 18 comprising a compound having a formula selected from

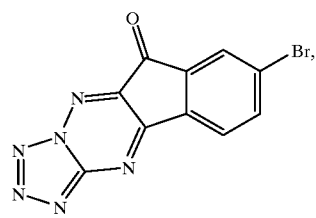

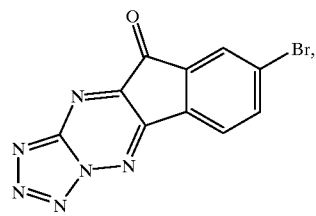

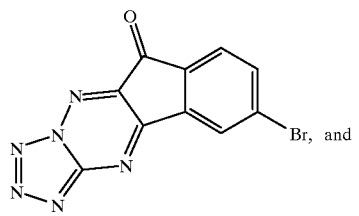

Br, and

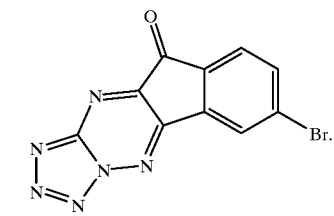

26. A composition of claim 18 comprising a compound having a formula selected from

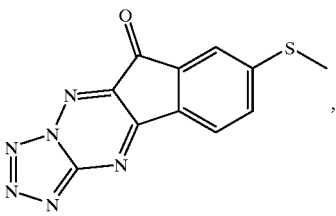

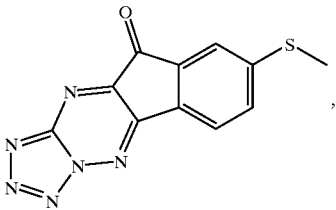

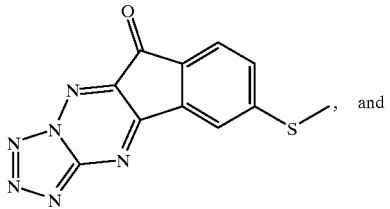

and

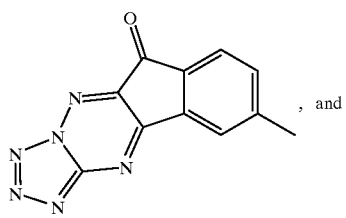
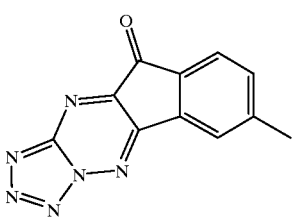
27. A composition of claim 18 comprising a compound having a formula selected from
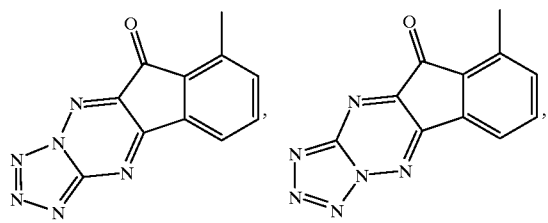
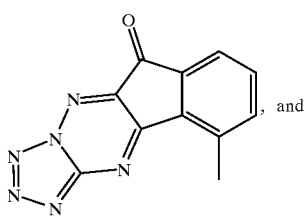
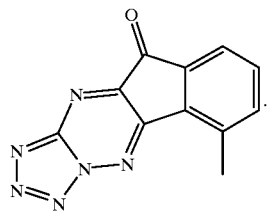
28. A composition of claim 18 comprising a compound having a formula selected from
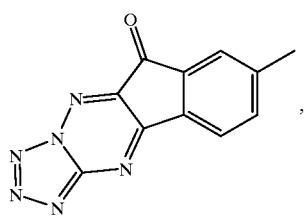
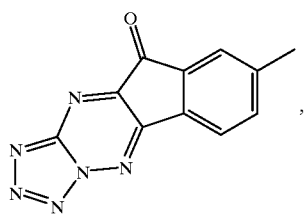
29. A composition of claim 18 comprising a compound having a formula selected from
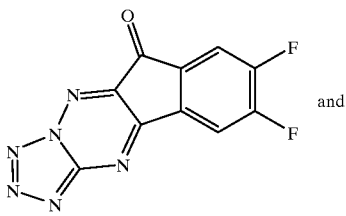
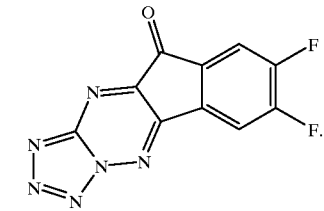
30. A composition of claim 18 comprising a compound having a formula selected from
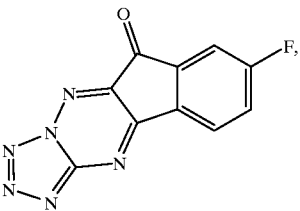
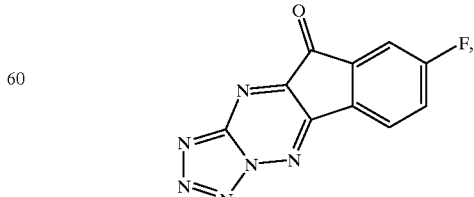

-continued

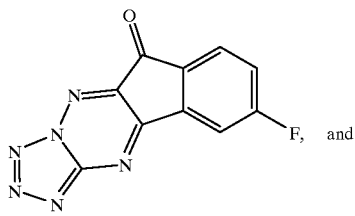

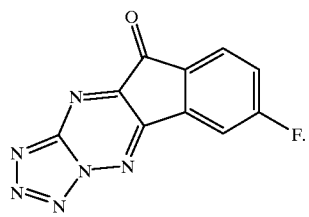

31. A composition of claim 18 comprising a compound having a formula selected from

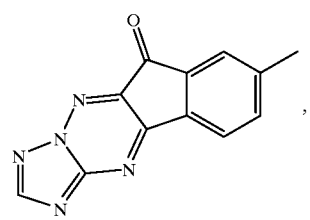

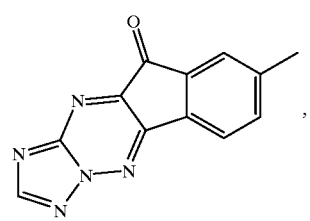

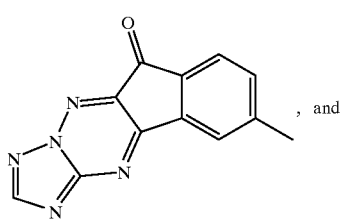

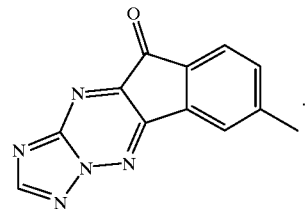

32. A composition of claim 18 comprising a compound having a formula selected from

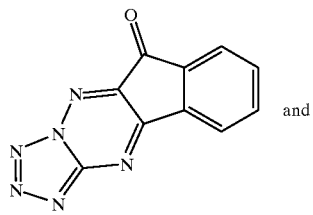

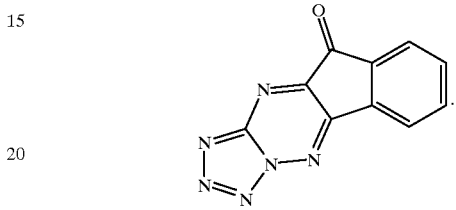

33. A composition of claim 18 comprising a compound having a formula selected from

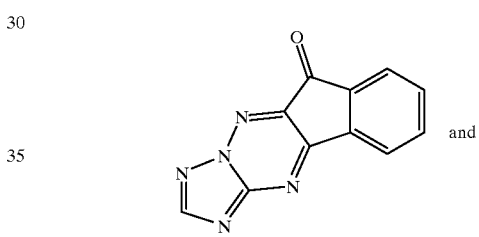

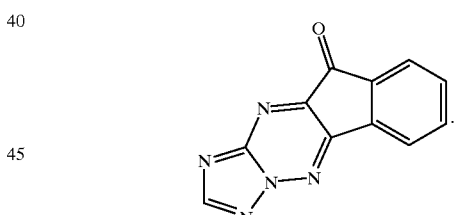

34. A composition of claim 18 comprising a compound having the formula

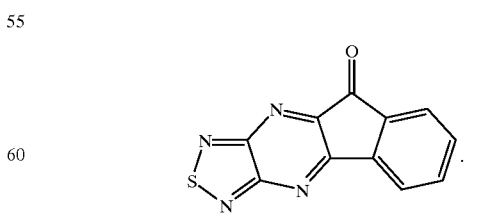

35. A composition of claim 18 wherein at least one of $R^1$, $R^2$, $R^3$ and $R^4$ is a heteroalkyl group selected from fluorine, chlorine, bromine and iodine.

36. A composition of claim 18 wherein $R^2$ and $R^3$ join together to form a compound as shown in the formula

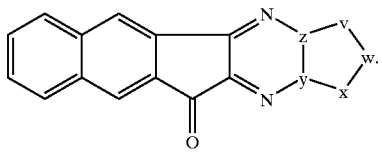

37. A composition of claim 18 wherein at least one of $R^1$, $R^2$, $R^3$ and $R^4$ is an alkyl group selected from $C_1$–$C_{15}$ alkyl.

38. A composition of claim 18 wherein at least one of $R^1$, $R^2$, $R^3$ and $R^4$ is an alkyl group selected from $C_1$–$C_6$ alkyl.

39. A method of inducing apoptosis in a cell wherein said method comprises contacting said cell with an effective dose of a composition according to claim 18.

* * * * *